United States Patent
Habar

(10) Patent No.: US 9,272,070 B2
(45) Date of Patent: Mar. 1, 2016

(54) ABSORBENT ARTICLE

(71) Applicant: MICROCAPSULES TECHNOLOGIES, Puiseaux (FR)

(72) Inventor: Gerard Habar, Bourron-Marlotte (FR)

(73) Assignee: Microcapsules Technologies, Puiseaux (FR)

( * ) Notice: Subject to any disclaimer, the term of this patent is extended or adjusted under 35 U.S.C. 154(b) by 170 days.

(21) Appl. No.: 14/198,218

(22) Filed: Mar. 5, 2014

(65) Prior Publication Data

US 2014/0257217 A1    Sep. 11, 2014

(30) Foreign Application Priority Data

Mar. 5, 2013  (FR) ..................... 13 51969

(51) Int. Cl.
| | |
|---|---|
| A61F 13/15 | (2006.01) |
| A61L 26/00 | (2006.01) |
| A61F 13/49 | (2006.01) |
| A61F 13/20 | (2006.01) |
| B01J 13/10 | (2006.01) |
| A61F 13/84 | (2006.01) |

(52) U.S. Cl.
CPC .............. *A61L 26/0066* (2013.01); *A61F 13/15* (2013.01); *A61F 13/15203* (2013.01); *A61F 13/20* (2013.01); *A61F 13/2071* (2013.01); *A61F 13/49* (2013.01); *A61L 26/0095* (2013.01); *B01J 13/10* (2013.01); *A61F 2013/8408* (2013.01); *A61F 2013/8438* (2013.01); *A61F 2013/8452* (2013.01)

(58) Field of Classification Search
CPC ........... A61F 13/15211; A61F 13/8405; A61F 2013/8408; A61F 2013/8414; A61F 2013/8438; A61F 2013/8441; A61F 2013/8447; A61F 2013/8452; A61L 15/46
See application file for complete search history.

(56) References Cited

U.S. PATENT DOCUMENTS

| | | | | |
|---|---|---|---|---|
| 3,691,271 A * | 9/1972 | Charle | ................. | A61K 8/0208 |
| | | | | 162/161 |
| 3,918,452 A * | 11/1975 | Cornfeld | .............. | A61K 9/0036 |
| | | | | 424/431 |
| 4,406,816 A | 9/1983 | Sliwka | | |
| 4,959,059 A * | 9/1990 | Eilender | ............... | A61F 5/4401 |
| | | | | 5/926 |
| 5,429,628 A | 7/1995 | Trinh et al. | | |
| 5,733,272 A | 3/1998 | Brunner et al. | | |
| 6,369,290 B1 | 4/2002 | Glaug et al. | | |
| 8,574,610 B2 * | 11/2013 | Code | .................. | A61F 13/8405 |
| | | | | 422/37 |
| 2003/0120224 A1 | 6/2003 | Geiser et al. | | |
| 2003/0120225 A1 | 6/2003 | Everhart et al. | | |
| 2005/0124947 A1 * | 6/2005 | Fernfors | ................. | A61F 13/42 |
| | | | | 604/361 |
| 2006/0229580 A1 * | 10/2006 | Raidel | ............... | A61F 13/47209 |
| | | | | 604/374 |
| 2007/0142804 A1 * | 6/2007 | Bernard | .................... | C08L 1/12 |
| | | | | 604/375 |
| 2009/0131890 A1 * | 5/2009 | Rourke | .................. | A61B 5/441 |
| | | | | 604/304 |
| 2011/0200654 A1 | 8/2011 | Habar | | |
| 2012/0191056 A1 * | 7/2012 | Nozaki | ................... | A61F 13/84 |
| | | | | 604/372 |
| 2014/0135722 A1 * | 5/2014 | Dougherty, Jr. | ........ | A61F 13/42 |
| | | | | 604/361 |

FOREIGN PATENT DOCUMENTS

| | | |
|---|---|---|
| EP | 0674942 | 10/1995 |
| EP | 2 468 309 | 6/2012 |
| FR | 2718059 A1 | 10/1995 |
| FR | 2787024 A1 | 6/2000 |
| FR | 2937248 A1 | 4/2010 |
| WO | WO 94/22500 | 10/1994 |
| WO | WO 94/22501 | 10/1994 |
| WO | WO-03/020240 A2 | 3/2003 |
| WO | WO 2005/120412 A1 | 12/2005 |
| WO | WO 2012/087891 A1 | 6/2012 |

OTHER PUBLICATIONS

French Search Report and Written Opinion for corresponding French Application No. FR 13 51969, dated Jan. 30, 2014.
English Language Translation of French Search Report and Written Opinion for corresponding French Application No. FR 13 51969, original document dated Jan. 30, 2014.

* cited by examiner

*Primary Examiner* — Lynne Anderson

(74) *Attorney, Agent, or Firm* — Jones Robb, PLLC

(57) ABSTRACT

An absorbent article can include, in an immobilized form:
a) microcapsules formed, in a proportion of at least 25% by weight relative to the total weight of polymer(s) forming the microcapsules, of a material derived from at least one natural polymer, a protein analog thereof, or a derivative thereof, and charged with at least one active agent, and
b) at least one release agent that is capable of stimulating the dissolution of the microcapsules during the placing of the absorbent article in contact with an aqueous medium, and chosen from enzymes, surfactants that are water-soluble at room temperature and atmospheric pressure, and mixtures thereof,
the microcapsules a) and the release agent b) being present in the said article in a form isolated from each other.

20 Claims, No Drawings

ABSORBENT ARTICLE

TECHNICAL FIELD

The present invention relates to the field of absorbent articles, especially hygiene articles, and in particular personal hygiene articles. The present invention more particularly relates to an absorbent article, especially a hygiene article, comprising, separately, on the one hand, specific microcapsules charged with at least one active agent and, on the other hand, at least one release agent that is capable of stimulating the release of the active agent present in the said microcapsules during the placing of the absorbent article in contact with an aqueous medium.

BACKGROUND

Absorbent personal hygiene articles are well known. Typical examples of such absorbent articles that may especially be mentioned include sanitary towels, pantiliners, tampons, articles for incontinent adults, baby nappies, etc.

These articles are commonly used for absorbing and retaining bodily fluids and other exudates excreted by the human body, such as urine and menstruations.

These absorbent personal hygiene articles may, however, lead to the appearance of irritation and/or allergy, especially in the case of people with sensitive skin, and/or on account of the presence of the bodily fluids and/or exudates, they may be perceived as being malodorous.

Consequently, many methods and materials for controlling and reducing these problems of irritation, allergy and/or unpleasant odours in absorbent articles have been developed.

With regard in particular to the problem of unpleasant odours, fragranced materials are widely used for this purpose, as are ingredients such as silica or zeolites which are capable of trapping some of the molecules that generate unpleasant odours.

A drawback commonly observed is the permanent manifestation of the odour of fragrance on the absorbent article and thus, before use of the said article, which, for obvious reasons, may not be acceptable to certain consumers.

In addition, owing to the continuous contact of the absorbent article with the external medium, another drawback encountered is impairment of the olfactory power, or even a change in the fragranced materials over time.

Techniques for controlling unpleasant odours which do not give a perceptible odour to the absorbent article before its use have already been proposed.

In this respect, mention may especially be made of documents WO 94/22500, WO 94/22501, WO 2005/120 412, U.S. Pat. No. 6,369,290, U.S. Pat. No. 5,733,272, U.S. Pat. No. 5,429,628 or WO 2012/087 891.

Finally, another drawback is the rate of release of the fragranced materials, which may occasionally be insufficient, to the point that a malodorous emission is nevertheless perceived.

Although absorbent personal hygiene articles on the market to date may be judged as being satisfactory with regard to the aspects mentioned above, the use of absorbent personal hygiene articles having further improved characteristics regarding these aspects, in particular in terms of rate of release of the active agent under consideration, remains a constant objective.

SUMMARY

The inventors have found that the use of an active agent encapsulated in specific microcapsules, in combination with a secondary active agent (referred to hereinbelow in the present application as a "release agent") directed towards stimulating the release of the said microencapsulated active agent under particular conditions, leads to an interesting alternative to the methods proposed to date.

Thus, according to a first of its aspects, the present invention relates to an absorbent article comprising, in an immobilized form:

a) microcapsules formed, in a proportion of at least 25% by weight and preferably at least 50% by weight relative to the total weight of polymer(s) forming the microcapsules, of a material derived from at least one natural polymer, a protein analogue thereof, or a derivative thereof, and charged with at least one active agent, and b) at least one release agent that is capable of stimulating the dissolution of the microcapsules during the placing of the absorbent article in contact with an aqueous medium, and chosen from enzymes, surfactants that are water-soluble at room temperature and atmospheric pressure, and mixtures thereof, the microcapsules a) and the release agent b) being present in the said article in a form isolated from each other.

Moreover, the present invention relates to an absorbent article comprising, in an immobilized form:

a) at least partially crosslinked microcapsules charged with at least one active agent, and b) at least one release agent that is capable of stimulating the release of the encapsulated active agent during the placing of the absorbent article in contact with an aqueous medium, and chosen from enzymes, surfactants that are water-soluble at room temperature and atmospheric pressure, and mixtures thereof, the microcapsules a) and the release agent b) being present in the said article in a form isolated from each other.

It is understood that the absorbent article such as above-defined reproduces all the considered features under its native form, that is to say before its use.

Thus, the term "before its use" or "ready for use" in the sense of the present invention intends to denote an absorbent article in its state such that it is prior to all contact with the bodily fluids and/or exudates excreted by the human body to absorb.

For the purposes of the present invention, the term "derived from at least one natural polymer, a protein analogue thereof, or a derivative thereof" is intended to denote the fact that the material may consist of one or more polymer(s) per se, but also of one or more compounds obtained after the partial or total crosslinking which may be considered in the technique for manufacturing the microcapsules according to the invention, as described below.

For the purposes of the present invention, the term "at least partially crosslinked microcapsules" is intended to denote microcapsules at least partly formed from at least one polymer which is only partly present in a crosslinked form. In other words, a part of the said polymer constituting the microcapsules is present therein in a non-crosslinked form.

Thus, the inventors have now found that the arrangement, in the same article, of particular microcapsules charged with active agent(s) and of a release agent that is reactive with regard to the material constituting all or part of these microcapsules proves to be particularly advantageous in several respects. Specifically, the presence of the release agent leads to a marked stimulation of the rate of release of the microencapsulated active agent and thus to a manifestation, within a short period, or even immediately, of the desired effect associated with this specific active agent.

First, the article permits controlled release of the active agent under consideration. Specifically, this active agent is released only once the said article comes into contact with the aqueous medium.

What is more, owing to the microencapsulated nature of the said active agent, it may conserve its integrity, and thus its efficacy, for longer.

For the purposes of the present invention, the term "absorbent article" is intended to denote any device that is capable of absorbing and retaining liquid media, especially physiological media, such as bodily exudates or fluids such as tears, nasal mucus, urine, sweat, menstruations and faecal matter.

Thus, examples of absorbent articles according to the invention may include nappies, infant nappies, clothes for incontinent adults and female hygiene clothing such as sanitary towels, pantiliners, sanitary tampons, interlabial devices, haemorrhoid cushions, etc.

However, the arrangement according to the invention is such that it may also be considered in absorbent articles such as, for example, sponges, wipes, handkerchiefs, etc.

According to another of its aspects, the present invention relates to the use of an article as defined above for controlling and/or reducing the unpleasant odours of bodily fluids and/or exudates excreted by the human body, in particular urine and menstruations.

According to yet another of its aspects, the present invention concerns the use of an article as defined above for controlling and/or reducing irritations, inflammations and/or infections associated with the said article and/or the said bodily fluids and/or exudates excreted by the human body.

DETAILED DESCRIPTION

Microcapsules

For the purposes of the invention, a "microcapsule" denotes a material entity of micrometric size having a "core/shell" architecture and whose shell or envelope surrounds the core, also known as the centre, in which are encapsulated one or more active agents.

This core may be featured by a cavity or may be of matrix nature.

The shell surrounding the core may optionally be of the same nature as the core, provided that it is suitable for encapsulating active agent(s).

Thus, microcapsules may be hollow (vesicular) or filled (matricial).

As illustrations of architectures of microcapsules that are already known, mention may be made especially of liposomes; microspheres or microbeads, which are particles consisting of a network of macromolecules, in which network is trapped the active substance in the form of molecules, micrometric solid particles or fine droplets of solution; or microcapsules, which are hollow particles surrounded by a more or less rigid wall.

The microcapsules that are more particularly under consideration according to the invention are microparticles "with a reservoir", i.e. having an architecture of "core/shell" type.

For obvious reasons, the nature of the microcapsules according to the invention is such that it is compatible with the intended use of an absorbent article according to the invention. In other words, the microcapsules are made of materials that are preferably inert with regard to the user, so as to avoid any undesirable effect, for instance allergies and/or irritations.

In addition, the nature of the microcapsules according to the invention is such that it is inert with regard to the active agents intended to be microencapsulated therein.

Finally, the nature of the microcapsules according to the invention is such that it is reactive with regard to the combined release agent.

For the purposes of the invention, "reactive" means that the placing in contact of the microcapsules or, at the very least, of the material forming the outer wall of this microcapsule or of at least one of the materials forming this wall, induces a loss of cohesion of the outer surface (or wall) of the microcapsules within a short time, or even immediately, thus bringing about the release of the microencapsulated active agent.

This loss of cohesion may be manifested in several ways, namely rupture, swelling, impairment or destruction.

The terms "rupture", "impairment" and "destruction" of the microcapsules thus mean, for the purposes of the present invention, the loss of cohesion of the wall of the said microcapsules, which may take place according to at least one of the following non-limiting mechanisms, namely solubilization, decomposition, disintegration, dissociation, separation, dissolution, fracturing, swelling, or increase in porosity, or even an extraction of the active agent by the release agent.

This mechanism may especially depend, on the one hand, on the nature of at least one of the materials forming the microcapsule and, on the other hand, on the nature of the associated release agent.

More specifically, this reactivity is reflected by a stimulation of the release of the encapsulated active agent.

For the purposes of the present invention, the term "stimulation" is intended to qualify an increase in the rate of loss of cohesion as defined above in the presence of at least one release agent conveyed by an aqueous medium, and thus of release of the said encapsulated active agent, when compared with the microcapsules according to the invention placed in contact only with the aqueous medium, i.e. in the absence of the release agent.

This increase in the rate of release of the microencapsulated active agent, which is generally significant, may vary depending on the degree of crosslinking of the microcapsule wall and by the choice and dose of the release agent.

The material(s) used for the manufacture of microcapsules according to the invention and the degree of crosslinking under consideration are such that the said microcapsules are preferably water-insensitive or, in other words, advantageously show prolonged mechanical resistance to water.

In other words, their impairment, and thus the release of the microencapsulated active agents, on contact with an aqueous medium not supplemented with a release agent according to the invention will be manifested only after a period that is significantly longer when compared with the period observed on contact with this same aqueous medium but supplemented with such a release agent.

As indicated previously, the microcapsules according to the invention are formed, in a proportion of at least 25% by weight and preferably at least 50% by weight, relative to the total weight of polymer(s) forming the microcapsules, of a material derived from at least one natural polymer, a protein analogue thereof, or a derivative thereof.

The choice of natural polymers is advantageous in view of their hydrophilic nature, or even their water-soluble nature, which facilities the manufacture of the microcapsules, especially via the microencapsulation techniques defined below.

Specifically, microcapsules consisting of "synthetic" material, for instance melamine formaldehyde, urea formaldehyde, polyurethane, acrylics, polyamide or silicone, are highly crosslinked microcapsules and are therefore sparingly sensitive to chemical products, in particular to water, even in the presence of a release agent according to the invention. Consequently, the use of microcapsules consisting solely of "synthetic" materials would lead to an excessively slow release of the microencapsulated active agent, despite the use of a release agent according to the invention.

Another advantage attached to natural polymers is that, once the microcapsules have been formed, especially via one of the microencapsulation techniques defined below, their degree of crosslinking, and thus their water sensitivity, may be very readily adapted according to the nature and amount of crosslinking agent(s).

The natural origin of the polymers under consideration in the present invention from which the material of the microcapsules intended to react with the release agent is liable to be derived is all the more advantageous since it satisfies a consumer demand in this direction.

Preferably, with the exception of the microencapsulated active agents, all the compounds forming the microcapsules according to the invention are of natural origin.

The nature of the natural polymer may especially be conditioned by the microencapsulation technique under consideration, as indicated below.

The natural polymer is preferably predominantly linear. This characteristic is advantageous in that it makes it possible to vary the water sensitivity of the said microcapsules.

As natural polymers that are suitable for making microcapsules in accordance with the invention, mention may be made especially of natural polymers of animal or plant origin.

Preferably, the natural polymers according to the invention may be chosen from amphoteric or cationizable natural polymers.

Even more preferably, the natural polymers according to the invention may be chosen from gelatin, chitin, polyosides or polysaccharides chosen from gum arabic, gum tragacanth, karaya gum, galactomannans derived from certain seeds, such as guar or locust bean, tara gum, pectins located in the cell walls and intracellular cements of plants, polyosides derived from bacterial fermentation, xanthan gum, gellan gum, scleroglucan gum, algal extracts, especially from red algae such as agar-agar and carrageenans, or brown algae such as alginates, a protein analogue thereof, or a derivative thereof, and mixtures thereof.

For the purposes of the present invention, the term "gelatin" is intended to denote any protein product obtained by partial hydrolysis of collagen extracted from skin, such as pig skin, or from bones, cartilage, ligaments, etc. More particularly, the gelatin results from a break of the molecular bonds between collagen strands, obtained by prolonged boiling and then solidification by cooling. When mixed with water, it forms a semi-solid colloidal gel.

For the purposes of the present invention, the term "chitin" is intended to denote a polysaccharide derived from the polymerization of N-acetylglucosamine bonded together via a bond of the β-1,4 type. This is an important structural molecule in many taxons of eukaryotes, especially fungi and arthropods.

For the purposes of the present invention, the term "protein analogue" is intended to denote any protein product having physical and chemical properties similar to a natural polymer according to the invention and having similar behaviour with regard to an aqueous medium and a release agent in the context of an absorbent article according to the present invention in terms of loss of cohesion, or even of disintegration.

As protein analogues of a natural polymer in accordance with the invention, mention may be made especially of plant proteins such as those extracted from soybean, lupine or wheat.

For the purposes of the present invention, the term "derivatives" is intended to denote any product having physical and chemical properties similar to the natural polymer from which it is obtained and having similar behaviour with regard to an aqueous medium and a release agent in the context of an absorbent article according to the present invention in terms of loss of cohesion, or even of disintegration.

As derivatives of a natural polymer in accordance with the invention, mention may be made especially of chitosan, cellulose derivatives such as carboxymethylcellulose, and modified starches.

Chitosan is a polyoside composed of the random distribution of D-glucosamine β-(1-4) bonded (deacetylated unit) and of N-acetyl-D-glucosamide (acetylated unit). It is produced by chemical deacetylation (in alkaline medium) or enzymatic deacetylation of chitin.

Preferably, the amphoteric natural polymer is featured by gelatin.

The amphoteric or cationizable natural polymer(s), a derivative thereof or a protein analogue thereof, preferably gelatin, generally have a gel force ranging from 120 bloom to 300 bloom, preferably from 130 bloom to 200 bloom and better still from 150 bloom to 180 bloom.

Moreover, in the light of the foregoing, the material derived from at least one natural polymer, a protein analogue thereof, or a derivative thereof, and intended to react with the release agent may constitute the sole component of the microcapsules.

However, microcapsules in accordance with the present invention may also use this material as a mixture with other compounds, referred to as associated compounds.

Such associated compounds that may especially be mentioned include synthetic polyacids such as polyacrylic or methacrylic acids or copolymers thereof, polyaspartic acid, and copolymers of polyvinylpyrrolidone and of maleic anhydride such as Gantrez.

The choice and proportion of this or these associated compound(s) are obviously adjusted so as not to adversely affect the desired properties associated with the microcapsules according to the invention. Also, the choice and proportion of this or these associated compound(s) may be conditioned by the microencapsulation technique under consideration. These adjustments clearly fall within the competence of a person skilled in the art.

Preferably, the material derived from at least one natural polymer, a protein analogue thereof, or a derivative thereof, may form the microcapsules to a proportion of at least 50% by weight, preferably of at least 60% by weight, more particularly of at least 70% by weight and better still of at least 80% by weight, relative to the total weight of polymer(s) forming the microcapsules.

As emerges from the foregoing, the microcapsules under consideration according to the invention are charged with one or more active agents of interest.

This may be performed via any known microencapsulation technique, provided that it is compatible with the nature of the material(s) under consideration for the microcapsules and the active agent(s) under consideration.

For the purposes of the invention, the term "microencapsulation" is thus intended to denote any process via which a solid, liquid or pasty product is enclosed in microcapsules.

The main processes for encapsulating at least one active agent in microcapsules are generally processes jointly involving the manufacture of the microcapsules and the encapsulation of the active agent under consideration in the said microcapsules.

As illustrations of encapsulation techniques using natural polymers as mentioned previously and which may be considered according to the invention, mention may be made especially of emulsification followed by evaporation or extraction of the solvent, double emulsification solvent evaporation/extraction, atomization (or "spray drying"), prilling, simple or complex coacervation, or the formation of LBL (layer by layer) self-assembled multilayer films.

The in situ polymerization of synthetic resins such as melamine, urea-formaldehyde, polyamide, acrylic or polyurethane resins may also be envisaged by incorporation of natural polymers.

The natural polymers that are preferred for the complex coacervation technique may be amphoteric or cationizable natural polymers, preferably chosen from gelatin, chitosan, cellulose derivatives, gum arabic and alginates, and mixtures thereof.

The natural polymers that are preferred for the spray drying or prilling technique may be nonionic, anionic or cationic natural polymers.

Thus, the natural polymers that are preferred for the spray drying technique may be cellulose derivatives or starch derivatives, and mixtures thereof.

The natural polymers that are preferred for the prilling technique may be alginates.

The final choice of the type of technique and of the nature of the microcapsules depends on the application and on factors such as the particle size, the thickness of the wall, the impermeability, the heat stability, the degradability, the compatibility and the adhesion to the environment of the final use.

The microencapsulated active agent according to the invention advantageously results from a coacervation microencapsulation, and better still from a complex coacervation microencapsulation.

The complex coacervation microencapsulation technique is in point of fact favoured given that it may be envisaged for the formulation of microcapsules from compounds of natural origin, especially gelatin, and whose transformation gives access to advantageous properties in terms of flexibility, transparency, natural adhesion, release, biodegradability, humidity, compatibility and pH.

Besides these advantages, the interest of this technique is that it makes it possible to obtain microcapsules that are sufficiently crosslinked to be sufficiently leaktight under the conditions of use and thereby sparingly sensitive to water and nevertheless to allow rapid release of the microencapsulated active agent under the influence of the release agent in the presence of an aqueous medium. This technique is thus particularly suited especially with regard to an active agent featured by a volatile product, for instance fragrances. It is this technique which also makes it possible to obtain the highest percentage of active agent in the microcapsules ("payload") relative to their total weight.

More generally, microcapsules resulting from a complex coacervation microencapsulation are formed by precipitation, in acidic medium, of a complex formed from at least one natural polymer, a protein analogue thereof, or a derivative thereof and from at least one polymer bearing anionic charges.

Different anionic polymers serve to improve the system and are also such that the microcapsules are isolated or form bunches, such as acrylic homopolymers and copolymers.

Preferably, the coacervate, once deposited around the drops of the emulsion, is then compacted by cooling and then crosslinked to make the reaction irreversible (prevent the redissolution in water of the envelope at basic pH).

The complex coacervation microencapsulation technique is especially documented in documents FR 2 718 059, FR 08 57111, U.S. Pat. No. 4,406,816 or EP 0 674 942.

Thus, the process described in document EP 0 674 942 proposes to form a suspension in an acidic aqueous phase of particles consisting of droplets of a hydrophobic liquid, the said droplets being coated with a coacervate formed from gelatin, polyacrylic acid and carboxymethylcellulose, to cool the whole in order to solidify the particle wall, and to crosslink the gelatin in order to fix the structure and make the process irreversible.

The microcapsules according to the invention are thus preferably obtained by means of a technique of complex coacervation microencapsulation of at least one amphoteric or cationizable natural polymer and of at least one polymer bearing anionic charges, the polymer bearing anionic charges also possibly being of natural origin.

Preferably, the polymer(s) bearing anionic charges may be chosen from polyacrylic acid, carboxymethylcellulose, alginates, synthetic polyacids and gum arabic, and mixtures thereof.

The crosslinking may be performed with a variable intensity, preferably by using an aldehyde, in particular glutaraldehyde or formaldehyde. This crosslinking step may be completed by the action of tannins or other crosslinking agents that are well known to those skilled in the art.

The more rigorous the crosslinking, the more the microcapsules become insensitive to chemical products, including water, enzymes and surfactants, and also become leaktight.

Thus, advantageously, when the microcapsules are obtained via the complex coacervation microencapsulation technique, the said technique also comprises, after the coacervation step, a step of crosslinking via an aldehyde, preferably glutaraldehyde, the aldehyde preferably being able to represent from 5% to 30% by weight and preferentially from 10% to 20% by weight relative to the total weight of amphoteric or cationizable natural polymer(s).

The microencapsulation technique under consideration for obtaining microcapsules in accordance with the invention may also be atomization (or "spray drying").

This microencapsulation technique is more particularly advantageous for gaining access to microcapsules, which, admittedly, are less leaktight than those obtained via the complex coacervation microencapsulation technique as defined above, but have improved water sensitivity, especially in the presence of a release agent, preferably a surfactant, as described below.

To obtain microcapsules according to this particular embodiment, the active agent to be encapsulated is sprayed in an atomization tower with at least one starch derivative or cellulose derivative or a natural or synthetic gum dissolved in water. The product which exits therefrom is more or less surrounded by a shell of variable thickness made of powder, which will be applied without the presence of water onto a suitable support.

The microcapsules according to the invention may be in isolated form (spherical) or agglomerated (clusters or bunches).

The outside diameter of the microcapsules, in isolated or agglomerated form, may preferably be between 0.5 µm and 1 mm or even between 2 and 10 µm.

Specifically, if they are too small, the microcapsules will be porous and will retain the active agent poorly. If they are too large, they will not have the necessary sensitivity since the surface of interaction with the release agent will be too small.

Release Agent

As indicated previously, the release agent is intended to interact with at least one of the materials constituting the microcapsules associated in an article in accordance with the invention, namely the natural polymer, a protein analogue thereof or a derivative thereof as described previously.

For obvious reasons, the choice of the release agent is conditioned by the choice of the material(s) of which the architecture of the microcapsules is composed.

As stated above, the reactivity of the microcapsules with regard to the release agent is reflected by the fact that the placing of the said release agent in contact with a microcapsule containing the said active agent brings about a loss of cohesion of the wall of the said microcapsule which may take place by solubilization, decomposition, disintegration, dissociation, separation, dissolution, fracturing, swelling or increase in porosity, or even an extraction of the active agent by the release agent, the consequence being more or less rapid release of the encapsulated active agent. Insofar as the release agent is localized separately from the associated microcapsules, this placing in contact can advantageously only take place when it is conveyed by an aqueous medium.

Moreover, for obvious reasons, the release agent must be inert with regard to the user, so as to avoid any undesirable effect, for instance allergies and/or irritations.

The release agent may be in a liquid or solid form. It must be able to be conveyed by an aqueous medium to the microcapsules in order to ensure the release of the microencapsulated active agent.

Preferably, the release agent may be chosen from enzymes, surfactants that are water-soluble at room temperature and atmospheric pressure, and mixtures thereof.

In aqueous medium, the surfactants swell the microcapsule wall and make it porous. They then participate in the extraction of the encapsulated active agent, which, under their influence, migrates from the interior of the microcapsule to the external medium.

An enzyme as sole release agent is advantageous when controlled release of the encapsulated active agent over a prolonged period is desired. This especially concerns cosmetic active agents, which are preferably non-volatile.

The enzyme may preferably be of protease or amylase type. The nature of the enzyme depends on the nature of the natural polymer under consideration for the manufacture of the microcapsules. Thus, a protease is suitable when the natural polymer is featured by a protein, in particular gelatin, and an amylase is suitable when the natural polymer is featured by a polysaccharide, in particular starch.

For example, when the natural polymer is featured by gelatin, the enzyme may advantageously be featured by Purafect OX Enzyme (Danisco US Inc.-Genencor Division).

More preferably, the release agent may be chosen from surfactants that are water-soluble at room temperature and atmospheric pressure, and better still from nonionic surfactants, anionic surfactants, amphoteric surfactants and cationic surfactants, and mixtures thereof.

The release agent may preferably be featured by at least one surfactant that is water-soluble at room temperature and atmospheric pressure, chosen from cocodimethylamine oxide, hydrogenated castor oil PEG-60, ethoxylated $C_{16-18}$ alcohols, $C_{12-18}$ fatty alcohol sulfates, and mixtures thereof, preferably hydrogenated castor oil PEG-60 and $C_{12-18}$ fatty alcohol sulfates, and better still $C_{12-18}$ fatty alcohol sulfates.

According to one particular embodiment, the release agent is featured by a combination of at least one surfactant and of at least one enzyme as described above.

This particular embodiment is advantageous in that it leads to further improving the release of the encapsulated active agent, especially in terms of speed and of amount released.

It is understood that the immobilization of the microcapsules and of the release agent on an absorbent article according to the invention may be obtained according to various techniques.

The choice of the appropriate technique for immobilizing the release agent clearly falls within the competence of a person skilled in the art.

It is obviously capable of varying with the size of the microcapsules, the chemical nature of the material of which all or part of the microcapsules are composed, the nature of the release agent and the nature of the material(s) forming the absorbent article or at the very least the layer(s) of the absorbent article on which the microcapsules and the release agent are intended to be immobilized.

For example, the operating techniques for promoting the functionalization of the article according to the invention with the microcapsules and the associated release agent may be of the type such as:
  immersion of the article, or at the very least the layer(s) of the absorbent article on which the microcapsules or the release agent are intended to be immobilized, in a bath containing the species to be immobilized; or
  spraying or vaporization of the species to be immobilized onto the surface of the article, or at the very least the layer(s) of the absorbent article on which the microcapsules or the release agent are intended to be immobilized.

Preferably, the immobilization of the microcapsules on at least one layer forming the absorbent article according to the invention requires the least possible supply of water. Examples of such techniques that may especially be mentioned include spraying, sprinkling of dry capsules or deposition by coating with a roll. In all cases, a binder may be added.

The immobilization of the release agent may advantageously be obtained by spraying in liquid form (solution in water) onto at least one of the layers forming an absorbent article according to the invention, followed by drying of the said layer.

Preferably, the release agent is immobilized on a layer that is different from that on which the microcapsules are immobilized.

Active Agent(s) Present in the Microcapsules

The microcapsules according to the invention are suitable for the encapsulation of a wide variety of active agents.

The nature of the active agents according to the invention is such that it is compatible with the intended use of an absorbent article according to the invention. In other words, the active agents are made of a material that is preferably inert with regard to the user, so as to avoid any undesirable effects, for instance allergies and/or irritations. The limiting factor is above all the compatibility of the active agent with the adopted encapsulation technique.

Thus, the microencapsulated active agent according to the invention advantageously has a solubility in water at 20° C. of less than 4% and preferably less than 1%.

Preferably, the microencapsulated active agent may be present in microcapsules according to the invention in a content of between 10% and 40% by weight and preferably between 25% and 35% by weight, relative to the total weight of the microcapsule suspension.

As non-limiting illustration of active agents that may be considered according to the invention, mention may be made especially of odorous active agents, deodorizing active agents, cosmetic active agents, disinfecting active agents, bactericide active agents, and mixtures thereof.

Preferably, the cosmetic active agent may be chosen from moisturizing active agents, calmative active agents and anti-irritant active agents, and mixtures thereof.

According to a particular embodiment, the active agent is an odorous or deodorizing active agent, in particular a fragrance.

According to another particular embodiment, the active agent used in the microcapsules according to the invention may be an anti-irritant active agent.

This embodiment is especially advantageous in the case of nappies for infants, whose skin is particularly sensitive and reactive.

According to yet another particular embodiment, the active agent used in the microcapsules according to the invention may be a moisturizing or calmative active agent, for instance oils, shea derivatives, avocado derivatives and vitamins, and mixtures thereof.

According to yet another embodiment, the active agent used in the microcapsules according to the invention may be a disinfecting active agent, for instance triclocarban, chlorinated derivatives (for example Dakin®), silver derivatives and silver, and mixtures thereof.

According to one embodiment, the active agent used in the microcapsules according to the invention may be a volatile active agent, especially with regard to odorous and deodorizing active agents.

For the purposes of the present invention, the term "volatile" is intended to denote any compound whose odour is perceptible in the surrounding atmosphere (i.e. less than 5 meters away) at room temperature and atmospheric pressure.

According to a particular embodiment, an absorbent article according to the invention may comprise different kinds of microcapsules which differ from each other in the nature of the active agent they contain.

Aqueous Medium

According to one embodiment, the aqueous medium intended for dissolving the microcapsules may be featured by water.

According to a more preferred embodiment, especially with regard to the intended use of an absorbent article according to the invention, the aqueous medium intended for dissolving the microcapsules may be featured by at least one bodily fluid and/or exudate.

Preferably, the bodily fluid and/or exudate may be featured by tears, nasal mucus, urine, menstruations, sweat and faecal matter, and mixtures thereof.

Additional Compound

According to a particular embodiment, an absorbent article according to the invention may also comprise any other active agent in a non-encapsulated form, providing that these additional active agents do not impair the properties associated with the compounds of the invention mentioned previously.

Examples of such active agents that may especially be mentioned include sodium bicarbonate, zeolite and essential oils. Sodium bicarbonate is advantageous in that it promotes the well-being of the skin by neutralizing pH modifications consecutive to the presence of bodily fluids and/or, where appropriate, of the microencapsulated specific active agent.

Article According to Exemplary Embodiments

Preferably, an absorbent article according to the invention may be disposable. The term "disposable" is used herein to describe absorbent articles which are not intended to be washed, restored or reused as absorbent article after a single use.

The absorbent articles are preferably disposable after a single use.

As mentioned previously, the present invention relates to an absorbent article before its use, namely before all contact of said absorbent article with the bodily fluids and/or exudates excreted by the human body to absorb, comprising microcapsules and at least one release agent present in said absorbent article in a form isolated from each other.

Thus, an article according to the invention comprises microcapsules, on the one hand, and at least one release agent, on the other hand.

According to a particular embodiment, an absorbent article according to the invention may be formed from a single layer, the microcapsules being immobilized on one of the surfaces, preferably on that which is the more in contact with the skin, and the release agent being immobilized on the other surface, preferably that which is the more in contact with the external medium.

According to another particular embodiment, an absorbent article according to the invention may also be formed from at least:
a first layer comprising at least the release agent, and
a second layer comprising at least the microcapsules.

According to a preferred variant of realization, the second layer may be arranged above the first layer. This arrangement is conditioned by the path liable to be taken by the aqueous medium, which, for obvious reasons, is essentially conditioned by the force of gravity of the earth, or even the capillary force of the materials of which at least one of the layers of the absorbent article is constituted.

This variant is in point of fact particularly advantageous in that it leads to a necessary placing in contact between the aqueous medium and the release agent before the placing in contact of this aqueous medium with the microcapsules. Thus, the movement of the aqueous medium through the absorbent article according to the invention leads to a concomitant movement of the release agent towards the microcapsules and thus to the reaction leading to an immediate release, and thus improved, especially in terms of speed, of the active agent present in the said microcapsules.

According to another embodiment, an absorbent article according to the invention may be formed from at least:
a first layer comprising at least the release agent,
a second layer comprising at least the microcapsules, and
further an intermediate layer arranged between the first and the second layer comprising, respectively, the release agent and the microcapsules.

Preferably, the intermediate layer is capable of allowing the passage of liquid media, especially physiological media. To satisfy this particular embodiment, the intermediate layer is preferably porous.

The intermediate layer may be a web, preferably a hydrophilic web, for isolating in dry form the first and second layers described above, but allowing their placing in contact in the presence of an aqueous medium.

However, and as indicated above, an absorbent article according to the invention may also be featured by a sponge, a handkerchief or a wipe.

An absorbent article according to the invention, especially given the layer system under consideration above, may advantageously be multi-layered and may especially comprise an upper layer, an absorbent core and a lower layer (except for those for internal use such as tampons).

The upper layer, the lower layer and the absorbent core may be formed from any material known to those skilled in the art. Such materials are especially described in EP 2 468 309.

The term "upper layer" is intended to denote the surface of the article intended to be worn in the direction of or close to the user's body.

The term "lower layer" is intended to denote the side opposite to the upper layer, namely the surface of the article intended to be worn towards or placed next to the user's underwear or clothing.

The lower layer is preferably impermeable to liquids, in particular to bodily fluids and exudates, and is preferably made from a thin plastic film, although other liquid-impermeable flexible materials may also be used.

For the purposes of the present invention, the term "flexible" is intended to denote materials that are supple and that can easily follow the general shape and contours of the human body. The lower layer is intended to prevent the bodily fluids or exudates absorbed and contained in the absorbent core from soiling the elements liable to come into contact with the absorbent article, such as sheets, trousers, pyjamas and underwear.

The lower layer may advantageously be permeable to sweat ("breathable" textile), while at the same time remaining impermeable to other bodily fluids and/or exudates.

In the light of the foregoing, the first layer comprising at least the release agent may be featured by the upper layer, the absorbent core or the lower layer, preferably the absorbent core or the upper layer, and better still the upper layer.

The second layer comprising at least the microcapsules may be featured by the upper layer, the absorbent core or the lower layer, preferably the absorbent core.

Throughout the description, including the claims, the term "comprising one" should be understood as being synonymous with "comprising at least one", unless otherwise specified.

The terms "between . . . and . . . " and "ranging from . . . to . . . " should be understood as being inclusive of the limits, unless otherwise specified.

The examples that follow are given as non-limiting illustrations of the invention. The percentages are expressed by weight of starting materials. The compounds are, depending on the case, cited as the chemical names or as the CTFA names (International Cosmetic Ingredient Dictionary and Handbook).

EXAMPLES

Example 1

Manufacture of Microcapsules in Accordance with the Invention 55 g of gelatin with a bloom value of about 160 are placed with stirring in one liter of deionized water at 40° C. The mixture is heated to between 40 and 50° C. until the gelatin has totally dissolved, and 18.5 g of acrylic acid homopolymer with a molecular weight of about 1800 (Coatex Gx) are then added. The pH is brought to 8 by adding 20% sodium hydroxide.

880 g of Jasmine fragrance are weighed out.

The organic phase and the aqueous phase are mixed with stirring and emulsified until particles with a mean diameter of between 5 and 6 micrometers are obtained.

The emulsion obtained previously and a solution of 17 g of carboxymethylcellulose with a viscosity of 250 mPa·s in 625 ml of deionized water are then mixed in a thermostatic reactor equipped with a stirrer.

The viscosity measurement is as defined in FR 2 718 059.

The temperature is raised to 60° C. and acetic acid is added so as to adjust the pH to 4.3. The coacervate is cooled to 8° C. and maintained at this temperature for 10 hours. Hardening of the walls is performed by adding 17 g of 50% glutaraldehyde with vigorous stirring.

The temperature is maintained at 8° C. for 16 hours with vigorous stirring before raising the pH to 7 at a temperature of 20° C.

The microcapsules obtained are perfectly isolated and have a solids content of 35% for a viscosity of only 20 mPa·s.

Example 2

Evaluation of the Effect of Surfactants as Release Agent on the Release of an Odorous Active Agent The tests are performed with G Jasmine microcapsules described in Example 1.

Four surfactants from different chemical families are tested, namely:

| No. | Commercial name | Supplier | INCI |
| --- | --- | --- | --- |
| 1 | Aromox MCDW | Genencor | Cocodimethylamine oxide |
| 2 | Eumulgin HRE 60 | Cognis | Hydrogenated castor oil PEG-60 |
| 3 | Lutensol AT50 | BASF | Ethoxylated $C_{16-18}$ alcohols |
| 4 | Sulfopon 1218G | Cognis | $C_{12-18}$ fatty alcohol sulfate, sodium salt |

Procedure

1—Dilute the G Jasmine microcapsules containing 35% fragrance of Example 1 twofold with tap water.

2—Spray a defined amount (about 1 gram) of diluted microcapsules onto a handkerchief of "tissue" type, taking care to distribute the microcapsules well over the entire handkerchief, 3—In parallel, spray the same weight of surfactants at 10% in water onto another handkerchief of "tissue" type, taking care to distribute the surfactants well over the entire handkerchief,

| No. | Test surfactant | Mass of microcapsules (in g) | Mass of surfactants (in g) |
| --- | --- | --- | --- |
| 1 | Aromox MCDW | 1.128 | 1.097 |
| 2 | Eumulgin HRE 60 | 1.102 | 1.16 |
| 3 | Lutensol AT50 | 1.113 | 1.181 |
| 4 | Sulfopon 12/186 | 1.069 | 1.047 |

4—Dry the handkerchiefs in open air,

5—Assemble the two handkerchiefs so that the sprayed faces are in contact and so that the handkerchief containing the surfactant is on top of the one containing the microcapsules, 6—Wet the handkerchiefs uniformly with 4 grams of water and flatten them using a grille, and 7—Smell, without touching the handkerchiefs, from a distance of a few centimeters and classify the handkerchiefs from those giving off the most fragrance to those which smell the least, the microcapsules giving off the most fragrance being those that react best with the surfactants and the water.

Results

The handkerchiefs are classified in an order of decreasing odour.

The following result is obtained: 4>2~3>1.

Consequently, all the surfactants used in this test allow very satisfactory release of the odorous active agent under consideration, with, however, an improved effect for the surfactants of Sulfopon 12/186 and Eumulgin HRE 60 type, and more particularly of Sulfopon 12/186 type.

Example 3

Evaluation of the Effect of the Surfactant Combined with an Enzyme as Release Agent on the Release of an Odorous Active Agent The procedure described in Example 2 is repeated, also taking into consideration the presence of an enzyme of protease type (Purafect OX Enzyme, Danisco US Inc.-Genencor Division) which is added to a proportion of 5% in the preexisting solutions of surfactants at 10% in water.

These tests are performed with G Hexanal 5 micron microcapsules made according to the process of Example 1, the Jasmine fragrance being replaced with a 50% solution of hexanal in isopropyl myristate.

| | Test surfactant | Enzyme | Mass of microcapsules (in g) | Mass of surfactants (in g) |
|---|---|---|---|---|
| 5 | Eumulgin HRE 60 | No | 1.295 | 1.151 |
| 6 | Eumulgin HRE 60 | Yes | 1.266 | 1.122 |
| 7 | Sulfopon 12/186 | No | 1.248 | 1.117 |
| 8 | Sulfopon 12/186 | Yes | 1.255 | 1.157 |

Results

The handkerchiefs are classified in an order of decreasing odour.

The following result is obtained: 8>6>7>5.

These results confirm that the presence of an enzyme associated with a surfactant makes the microcapsules even more water-sensitive. What is more, these results confirm that the presence of a surfactant allows very satisfactory release of the odorous active agent under consideration, with a further improved effect for the surfactant Sulfopon relative to the surfactant Eumulgin.

Example 4

Evaluation of the Effect of the Microcapsules on the Release of an Odorous Active Agent The procedure described in Example 3 is repeated. The surfactant under consideration is Sulfopon 12/186. The microcapsules are those identified in the table and references (1) to (4) below.

| Type of microcapsules | Fragrance | Diameter (in μm) | Mass of surfactants (in g) | Mass of microcapsules (in g) |
|---|---|---|---|---|
| Gelatin (1) | Flax blossom | 5 | 1.332 | 1.335 |
| Gelatin (2) | Flax blossom | 6 | 1.326 | 1.260 |
| Silicone (3) | Flax blossom | 4 | 1.242 | 1.241 |
| Melamine (4) | Flax blossom | 6 | 1.326 | 1.266 |

(1) Microcapsules described in Example 1 of FR 2 718 059 (crosslinking step limited to glutaraldehyde. More precisely, second step using chromium alum not repeated).
(2) Microcapsules described in Example 1 of FR 2 718 059.
(3) Microcapsules described in Example 3 of FR 08 57111.
(4) Microcapsules described in Example 1 of U.S. Pat. No. 4,406,816 in which a fragrance replaces the described internal phase.

Results

The handkerchiefs are classified in an order of decreasing odour.

The following results are obtained: (1)>(2)>>(3)>(4).

The microcapsules of melamine and silicone do not have any smell. They are therefore entirely insensitive to water, even in the presence of the surfactant and of the enzyme.

On the other hand, the gelatin microcapsules are particularly satisfactory for ensuring rapid release of the odorous active agent under consideration.

What is claimed is:

1. Absorbent article comprising, in an immobilized form:
   a) microcapsules formed, in a proportion of at least 25% by weight relative to the total weight of polymer(s) forming the microcapsules, of a material derived from at least one natural polymer, a protein analogue thereof, or a derivative thereof, and said microcapsules being charged with at least one active agent, and
   b) at least one release agent that is capable of stimulating the dissolution of the microcapsules during the placing of the absorbent article in contact with an aqueous medium, and selected from the group comprising enzymes, surfactants that are water-soluble at room temperature and atmospheric pressure, and mixtures thereof, the microcapsules a) and the release agent b) being present in the said article in a form isolated from each other.

2. Article according to claim 1, wherein the microcapsules are obtained by means of a technique of complex coacervation microencapsulation of at least one amphoteric or cationizable natural polymer and of at least one polymer bearing anionic charges.

3. Article according to claim 2, wherein the complex coacervation microencapsulation technique further comprises, after the coacervation step, a step of crosslinking via an aldehyde, preferably glutaraldehyde, the aldehyde preferably representing from 5% to 30% by weight relative to the total weight of amphoteric or cationizable natural polymer(s).

4. Article according to claim 2, wherein the amphoteric or cationizable natural polymer(s) are selected from the group comprising gelatin, chitin, a protein analogue thereof, or a derivative thereof, and mixtures thereof.

5. Article according to claim 2, wherein the polymer(s) bearing anionic charges are selected from the group comprising polyacrylic acid, carboxymethylcellulose, alginates, synthetic polyacids, arabic gum, and mixtures thereof.

6. Article according to claim 1, wherein the material derived from at least one natural polymer, a protein analogue thereof, or a derivative thereof, forms the microcapsules to a proportion of at least 50% by weight, relative to the total weight of polymer(s) forming the said microcapsules.

7. Article according to claim 1, wherein the microencapsulated active agent represents a content of between 10% and 40% by weight, relative to the total weight of the microcapsule suspension.

8. Article according to claim 1, wherein the release agent is selected from the group comprising nonionic, anionic, cationic and amphoteric surfactants, and mixtures thereof.

9. Article according to claim 1, wherein the release agent is featured by at least one surfactant that is water-soluble at room temperature and atmospheric pressure, selected from the group comprising cocodimethylamine oxide, hydrogenated castor oil PEG-60, ethoxylated $C_{16-18}$ alcohols, $C_{12-18}$ fatty alcohol sulfates, and mixtures thereof.

10. Article according to claim 1, wherein the release agent is featured by at least one enzyme selected from the group comprising proteases when the natural polymer is featured by a protein, amylases when the natural polymer is featured by a polysaccharide, and mixtures thereof.

11. Article according to claim 1, wherein the aqueous medium is featured by at least water or a bodily fluid and/or exudates.

12. Article according to claim 1, wherein the microencapsulated active agent is selected from the group comprising at least one odorous active agent, a deodorizing active agent, a disinfecting active agent, a bactericide active agent, a cosmetic active agent, and mixtures thereof.

13. Article according to the claim 12, wherein the cosmetic active agent is selected from the group comprising at least one moisturizing active agent, a calmative active agent, an anti-irritant active agent, and mixtures thereof.

14. Article according to claim 1, wherein the said article is formed from at least:
   a first layer comprising at least the release agent, and
   a second layer comprising at least the microcapsules.

15. Article according to the claim 14, wherein the second layer is arranged above the first layer.

16. Article according to claim 14, wherein the said article further comprises at least one intermediate layer arranged between the first and the second layer, the said intermediate layer preferably being capable of allowing the passage of liquid media, especially physiological media, in particular by means of pores.

17. Article according to claim 1, wherein the said article is a sanitary towel, a pantiliner, a tampon, an article for incontinent adults or a baby nappy.

18. Method for controlling and/or reducing the unpleasant odours of bodily fluids and/or exudates excreted by the human body, said method comprising at least the step of contacting said bodily fluids and/or exudates excreted by the human body with an absorbent article as defined in claim 1.

19. Method for controlling and/or reducing irritations, inflammations and/or infections associated with an absorbent article as defined in claim 1 and/or with the bodily fluids and/or exudates excreted by the human body said method comprising at least the step of contacting said bodily fluids and/or exudates excreted by the human body with said absorbent article.

20. Absorbent article comprising, in an immobilized form:
   a) at least partially crosslinked microcapsules charged with at least one active agent, and
   b) at least one release agent that is capable of stimulating the release of the encapsulated active agent during the placing of the absorbent article in contact with an aqueous medium, and selected from the group comprising enzymes, surfactants that are water-soluble at room temperature and atmospheric pressure, and mixtures thereof, the microcapsules a) and the release agent b) being present in the said article in a form isolated from each other.

* * * * *